United States Patent [19]

Kondo et al.

[11] Patent Number: 5,104,973
[45] Date of Patent: Apr. 14, 1992

[54] METHOD FOR PURIFYING AND ISOLATING CARBOXYL-TERMINAL PEPTIDES

[75] Inventors: Jun Kondo, Machida; Chiharu Ohuchi, Yokohama, both of Japan

[73] Assignee: Mitsubishi Kasei Corporation, Tokyo, Japan

[21] Appl. No.: 321,222

[22] Filed: Mar. 9, 1989

[30] Foreign Application Priority Data

Mar. 15, 1988 [JP] Japan .................................. 63-60698

[51] Int. Cl.$^5$ ........................ C07K 17/06; C07K 1/14; G01N 33/00
[52] U.S. Cl. ................................... 530/334; 530/344; 530/345; 436/89; 436/90
[58] Field of Search ....................... 530/334, 344, 345; 436/89, 90

[56] References Cited

FOREIGN PATENT DOCUMENTS 2083477 9/1981 Fed. Rep. of Germany .

OTHER PUBLICATIONS

European Search Report.

*Primary Examiner*—Douglas W. Robinson
*Assistant Examiner*—Jon P. Weber
*Attorney, Agent, or Firm*—Oblon, Spivak, McClelland, Maier & Neustadt

[57] ABSTRACT

This invention provides a method for purifying and isolating a carboxyl-terminal peptide. A peptide bond between a lysine residue in a polypeptide and the adjacent amino acid residue is specifically cleaved on its carboxyl-terminal side. The resulting peptide mixture is then reacted with a solid carrier possessing on its surface functional groups capable of reacting and covalently bonding with free amino groups. Subsequently the peptide bond between the aminoterminal amino acid residue and the adjacent amino acid residue of each peptide is cleaned by acid treatment, and the peptides thus released from the solid carrier are isolated.

1 Claim, 2 Drawing Sheets

METHOD FOR PURIFYING AND ISOLATING CARBOXYL-TERMINAL PEPTIDES

BACKGROUND OF THE INVENTION AND PRIOR ARTS

The present invention relates to a method for purifying and isolating carboxyl-terminal peptides from its original polypeptide by a simple procedure.

Since the development of the Edman method for sequentially determining the sequence of amino acid residues of a polypeptide from its N-terminal in 1950 (P. Edman, Acta Chem. Scand., 4, 283 (1950)), various improvements have been made in the above method. Today N-terminal sequence analyses can be accomplished even with trace amounts of a sample at a picomolar level using an automatic sequencer (Experimental Techniques in Biochemistry, Second Series, 2. Chemistry of Protein (A), pp. 247-373, Ed. Jpn. Soc. Biochem., 1987, Tokyo Kagaku Dojin).

Meanwhile, with the advent of genetic engineering techniques in recent years, it has become most usual to estimate the whole amino acid sequence of polypeptides by determining the base sequence of a DNA complementary to a messenger RNA. In ordinary circumstances, however, the base sequence of the complementary DNA may be screened by using as a probe an oligonucleotide prepared on the basis of a determined amino acid sequence for a part of a desired polypeptide. In such cases, the screening of the above base sequence could be carried out with greater ease if the probe corresponded to the amino acid sequence close to a carboxy-terminal of the polypeptide. Furthermore, polypeptides may be actually biosynthesized with processing and often lack a part of a whole amino acid sequence coded by the messenger RNA. It is of prime importance, accordingly, to determine both the amino- and carboxyl-terminals of the polypeptide.

As analyses of a carboxyl-terminal amino acid, a hydrazinolysis method, a tritium labeling method and a carboxypeptidase method are currently employed (Experimental Techniques in Biochemistry, Second Series, 2. Chemistry of Protein (A), p. 230, Ed. Jpn. Soc. Biochem., 1987, Tokyo Kagaku Dojin).

Of these methods, the hydrazinolysis method and the tritium labeling method can only determine the amino acid residue at a carboxyl-terminal. Eventually, they can give no useful information for preparing the probe, and afford only data which are unreliable for identifying the position of amino acid residues coded by the messenger RNA. The carboxypeptidase method comprises sequentially cleaving peptide bonds of a polypeptide by various carboxy-peptidases from its carboxyl-terminal and following the time course of the changes in the cleavage thus prepared. This method, consequently, has disadvantages of (1) being cumbersome, (2) requiring relatively a large amount of sample, (3) involving uncertainty in the residue sequencing, and (4) being inadequate for analysis of relatively long-chain polypeptides.

SUMMARY OF THE INVENTION

The present inventors have accomplished this invention during the course of their strenuous search for a method of carboxyl-terminal amino acid sequence analysis that could derive much reliable information using such a slight amount of sample as that in the amino-terminal sequence analysis, in order to overcome the above disadvantages.

The present invention relates to a method for purifying and isolating a carboxyl-terminal peptide, characterized by specifically cleaving a peptide bond between a lysine residue in a polypeptide and the adjacent amino acid residue on its carboxyl-terminal side, by allowing the resulting peptide mixture to react with a solid carrier possessing on its surface functional groups capable of reacting and covalently bonding with free amino groups, subsequently cleaving the peptide bond between the amino-terminal residue and the adjacent residue of each peptide by acid treatment, and then by collecting the peptides thus released from the solid carrier

DETAILED DESCRIPTION OF THE INVENTION

Figure 1:
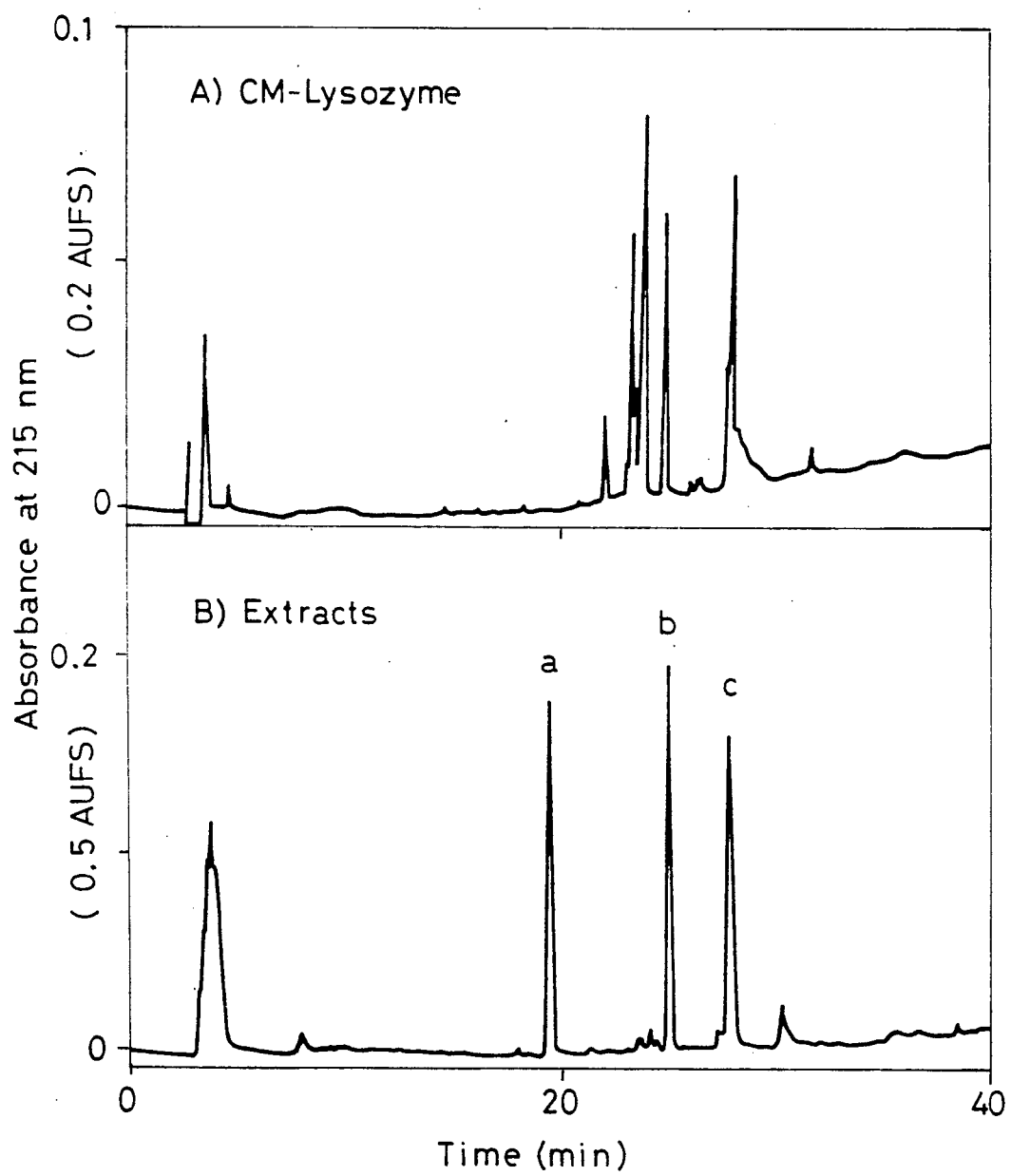
FIGS. 1 and 2, illustrate reversed phase high-performance liquid chromatographic charts of the peptides treated in Examples 1 and 2, respectively.

This invention takes the advantage of the facts that while the carboxyl-terminal peptide may bind to the above solid only via the α-amino group at its amino-terminal, other peptides may bind to the solid not only via the α-amino group at their amino-terminals but via the ε-amino group of their lysine residues as well, and that since only the peptide bond between the amino-terminal residue and the adjacent residue may be cleaved on treatment of the peptide-solid conjugate thus obtained with an appropriate acid under appropriate conditions, the carboxyl-terminal peptide may be released on the acid treatment into a reaction medium with its amino-terminal residue left behind on the solid surface.

The most useful method to specifically cleave the peptide bond between the lysine residue in the peptide and the adjacent amino acid residue on its carboxyl-terminal side is to use *Achromobacter lyticus* protease I [lysyl endopeptidase (EC 3.4.21.50), hereinafter referred to as API]. This enzyme is highly specific for cleaving a Lys-X linkage (where X denotes an amino acid residue), with a great rarity of non-specific cleavage (Experimental Techniques in Biochemistry, Second Series, 2. Chemistry of Protein (A), p. 262, Ed. Jpn. Soc. Biochem., 1987, Tokyo Kagaku Dojin). API may, therefore, be most preferably used in the present invention. The cleavage conditions with API are not much restricted because the enzyme is very stable. The enzyme may be added at a molar ratio between 1/20 and 1/2000, more preferably between 1/200 and 1/600, to the peptide to be cleaved, and incubated in a buffer solution at pH between 6 and 11, more preferably between 8 and 10.5, and at a temperature between 4 and 50° C., or more desirably between 20 and 45° C., for 1 to 50 hours, or more preferably for 4-8 hours. Any of the variety of buffer solutions commonly used in biochemical experiments may be used for the cleavage reaction in the invention. In consideration of a possible influence upon the following procedure, nevertheless, buffer solutions devoid of free amino groups are preferable, N-ethylmorpholine which is frequently used for Edman degradation being most preferable. Furthermore, it is also desirable to loosen a higher-order structure of the polypeptide without causing the loss in API activity, in order to promote the cleavage reaction.

Urea, for example, may be added at a concentration of 4-5 M for this purpose.

Besides API, Endoproteinase Lys-C (trade name) produced by *Rhizobacter enzymogenes* (Boehringer-Mannheim) may also be used.

Trypsin is a proteolytic enzyme specific for lysine and arginine residues. Accordingly, trypsin may be also used in the present invention in the same manner as API, provided that arginine residues have been previously modified with cyclohexane-1,2-dione, for example, according to the method described in "Sequencing of Proteins and Peptides", G. Allen, pp. 57-58, 1981, North-Holland Publishing Company, Amsterdam: New York. Oxford.

A wide variety of functional groups can be mentioned as those capable of reacting and covalently bonding with free amino groups, such as imide group, isourea, aldehyde group, cyano group, acetyl group, succinyl group, maleyl group, acetoacetyl group, dinitrophenyl group, trinitrobenzenesulfonate group, and isothiocyanate group. Among them, isothiocyanate group is best suited for the present invention in that it reacts only with an amino group and in that its linkage with $\epsilon$-amino group may be stable even under the acid treatment conditions where Edman degradation proceeds. The solid possessing functional groups such as isothiocyanate group may be prepared according, for example, to the method described in "Sequencing of Proteins and Peptides", G. Allen, p. 208, 1981, North-Holland Publishing Company, Amsterdam: New York. Oxford. Such substances as porous glass, silica gel and polystyrene may be used as a solid carrier of the present invention. Porous glass with an uniform fine pore size is particularly preferable because it is hydrophilic and its reaction may be easily controlled. Polystyrene, a hydrophobic carrier, may be rendered easier-to-use by increasing its hydrophilicity by, for example, means of introducing glucosaminol group into the isothiocyanate group (Iwanaga et al., Protein.Nucleic Acid.Enzyme 15 (10), 1052 (1970)). A coupling reaction of the solid possessing the functional group with the peptide mixture may be carried out at pH between 7 and 12, preferably between 9 and 11, and more preferably between 9.5 and 10.5, and at a temperature between 4 and 80° C., preferably between 10 and 60° C., for 5 minutes to 3 hours. It is desirable to eliminate oxygen from a reaction medium by replacing it with nitrogen throughout the course of the reaction. After completion of the coupling reaction, the peptide-solid conjugate is washed with an appropriate volatile solvent, e.g. acetonitrile or propanol, then allowed to dry, and subjected to acid treatment. That is, a small amount of acid barely enough to immerse the dried peptide-solid conjugate therein is added and the resulting mixture is incubated in a nitrogen atmosphere at 20 to 80° C., preferably at 30 to 60° C., for 5 to 60 minutes. For this acid treatment, trifluoroacetic acid, heptafluoroacetic acid, hydrochloric acid-saturated acetic acid, or other acids may be used. Among them, trifluoroacetic acid with which side reactions are rare is best suited. Upon completion of the reaction, a peptide-dissolvent, volatile solvent such as acetonitrile or propanol is added to the reaction mixture. Then a solid phase is removed to isolate the desired carboxyl-terminal peptide in a liquid phase. The carboxyl-terminal peptide thus isolated may be structurally determined in an usual manner by an amino acid composition analysis and by amino acid sequence analysis, or may also be used for other purposes intended.

In accordance with the present invention, it can be accomplished with a simple procedure to purify and isolate a carboxyl-terminal peptide from a polypeptide, and with ease to determine the structure of the carboxyl-terminal peptide of the polypeptide.

The present invention will be further illustrated by the following non-limiting examples.

EXAMPLE 1

Egg white lysozyme was reduced with $\beta$-mercaptoethanol and allowed to react with monoiodoacetic acid in an usual manner for carboxymethylation of a thiol group of its cystein residue. Two nanomoles of the carboxymethylated lysozyme were dissolved in 50mM N-ethylmorpholine-acetic acid buffer (pH 9.0) containing 5M urea. After having 10 picomoles of API, the solution was incubated for reaction for 6 hours at 37° C.. Following completion of the reaction, the reaction mixture was adjusted to pH 10.0 by adding 50mM N-ethylmorpholine aqueous solution, and 50 mg of DITC-CPG (phenylene diisothiocyanate bound to controlled pore glass; Sigma Chemical Company, St. Louis, Mo., USA) were added. The reaction system was then replaced with nitrogen and subjected to a coupling reaction for 1 hour at a room temperature with a constant agitation. Upon completion of the coupling reaction, the solid phase was washed with a 50% acetonitrile-2-propanol mixture (volume ratio, 3:7) containing 0.1% trifluoroacetic acid, and dried in vacuo. The dried solid phase was then mixed with 50 $\mu$l trifluoroacetic acid and incubated in a nitrogen atomosphere for 15 minutes at 40° C.. Subsequently, a 50% acetonitrile-2-propanol mixture (volume ratio, 3:7) containing 0.1% trifluoroacetic acid was added to the mixture, and centrifuged. The resulting supernatant was collected and dried in vacuo. The carboxyl-terminal peptides thus obtained were subjected to reverse phase high-performance liquid chromatography. This was carried out on an Octyl column (Bakerbond); 4.6 mm $\phi \times$ 250 mm, eluting with a 0-60% acetonitrile gradient at a flow rate of 1 ml/min. and using as a solvent acetonitrile aqueous solution containing 0.1% trifluoroacetic acid. FIG. 1, B shows a chromatogram thus obtained. Peak b was noted to coincide with an expected carboxyl-terminal peptide as a result of amino acid composition analysis (ninhydrin method) and amino acid sequence analysis (automatic Edman degradation) (Table 1). (There was no evidence of an amino-terminal residue of the said peptide in the extract, as anticipated.) Analyses of peaks a and c revealed the absence of amino acids, thus indicating that they are not peptides. Shown in FIG. 1, A) is a chromatogram of the peptide mixture obtained upon digestion with API.

TABLE 1

| Amino acid composition | | |
|---|---|---|
| Asp | 1.0 | (1) |
| Thr | 1.0 | (1) |
| Ser | | |
| Glu | 1.0 | (1) |
| Pro | | |
| Gly | 1.1 | (1) |
| Ala | 1.0 | (1) |
| Cys* | 1.0 | (1) |
| Val | 1.0 | (1) |
| Met | | |
| Ile | 0.9 | (1) |
| Leu | 1.1 | (1) |
| Tyr | | |
| Phe | | |
| Lys | | |

TABLE 1-continued

| | | |
|---|---|---|
| His | | |
| Arg | 1.9 | (2) |
| Trp | | (1) |
| Total | | (12) |
| Yield | 36.2% | |
| Amino acid sequence | | |
| TDVQAWIRGC*RL | | |

*Determined as carboxymethylcysteine.

EXAMPLE 2

Figure 2:
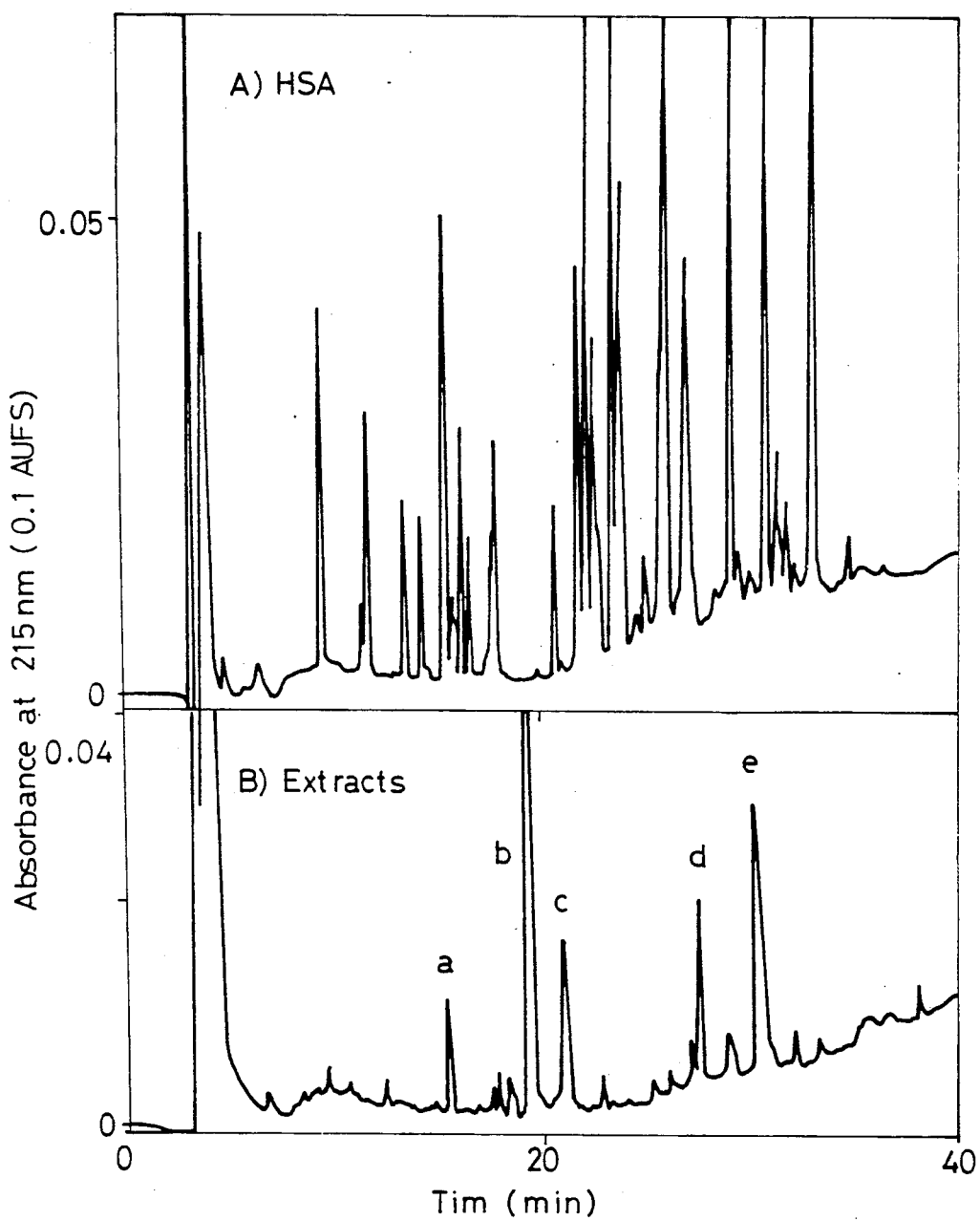

0.5 nanomoles of human serum albumin were subjected to digestion with API in the same manner as in Example 1 above, followed by the same procedure as in Example 1 above. The peptide thus isolated was analyzed as in Example 1 above, with the results depicted in FIG. 2, B). Analyses of peak C revealed an amino acid composition and amino acid sequence which were in accord with what had been expected. Peaks a, b, d, and e proved not to be peptides.

TABLE 2

| Amino acid composition | | |
|---|---|---|
| Asp | | |
| Thr | | |
| Ser | 1.0 | (1) |
| Glu | 1.1 | (1) |
| Pro | | |
| Gly | 1.1 | (1) |
| Ala | 3.9 | (4) |
| Cys | | |
| Val | 1.1 | (1) |
| Met | | |
| Ile | | |
| Leu | 2.0 | (2) |
| Tyr | | |
| Phe | | |
| Lys | | |
| His | | |
| Arg | | |
| Trp | | |
| Total | | (10) |
| Yield | 43.4% | |
| Amino acid sequence | | |
| VAASQAALGL | | |

What is claimed is:

1. A method for purifying and isolating carboxyl-terminal peptides, comprising specifically cleaving a peptide bond between a lysine residue in a polypeptide and the adjacent amino acid residue on its carboxyl-terminal side, reacting the resulting peptide mixture with a solid carrier possessing on its surface functional groups capable of reacting and covalently bonding with free amino groups, subsequently cleaving the peptide bond between the amino-terminal amino acid residue and the adjacent amino acid residue of each peptide by acid treatment, and then collecting the peptides thus released from the solid carrier.

* * * * *